United States Patent [19]

Boniort et al.

[11] Patent Number: 5,241,279
[45] Date of Patent: Aug. 31, 1993

[54] MICROWAVE MEASURING APPARATUS FOR CONTINUOUSLY AND WITHOUT CONTACT MEASURING THE THICKNESS OF A THIN CONDUCTING LAYER OF A RUNNING INSULATING SUPPORT SUCH AS A FIBER OR A TAPE

[75] Inventors: Jean-Yves Boniort, Limours; Georges Roussy, Laxou, both of France

[73] Assignee: Alcatel N.V., Netherlands

[21] Appl. No.: 858,599

[22] Filed: Mar. 27, 1992

[30] Foreign Application Priority Data

Mar. 29, 1991 [FR] France ................ 91 03878

[51] Int. Cl.⁵ ................ G01R 27/04; H01P 7/00
[52] U.S. Cl. ................ 324/636; 324/632; 324/635; 333/219
[58] Field of Search .............. 324/632, 633, 635, 636, 324/637; 333/219, 227, 202 HC

[56] References Cited

U.S. PATENT DOCUMENTS

| | | |
|---|---|---|
| 2,491,418 | 12/1949 | Schlesman . |
| 2,548,598 | 4/1951 | Feiker . |
| 3,401,333 | 9/1968 | Thompson . |
| 3,710,243 | 1/1973 | Keenan ................ 324/632 |
| 4,571,544 | 2/1986 | Walton ................ 324/636 |
| 4,841,223 | 6/1989 | Baum et al. ................ 324/632 X |
| 4,977,383 | 12/1990 | Niikanen ................ 333/219 |

FOREIGN PATENT DOCUMENTS 3107675  9/1982  Fed. Rep. of Germany .
3927394  2/1991  Fed. Rep. of Germany .
1106185  3/1968  United Kingdom .

OTHER PUBLICATIONS

IEEE Transactions on Instrumentation and Measurement, Mar. 1, 1974, pp. 100-101; M. A. Rzepecka: "A Microwave System for Measurement of the Diameter of Thin Electric Fibers".

Fossheim et al, "Broadband Tuning of Helical Resonant Cavities", J. Phys. E. Sci. Instrum., vol. 11, Sep. 1978, 892–893.

*Primary Examiner*—Gerard R. Strecker
*Assistant Examiner*—Diep Do
*Attorney, Agent, or Firm*—Sughrue, Mion, Zinn, Macpeak & Seas

[57] ABSTRACT

Apparatus for measuring continuously and without contact the thickness of a thin conducting layer on a running insulating support of the fiber or tape kind, wherein the apparatus includes:

a microwave generator associated by coupling means to a resonant cavity comprising a metal wire in the form of a helix which is fixed at its ends to two metal plates, said insulating support being suitable for running substantially along the axis of said helix; and means for coupling said cavity to a detection device for detecting the transmission factor of said cavity, which factor is directly a function of said thickness, said measurement being performed at constant frequency.

6 Claims, 3 Drawing Sheets

MICROWAVE MEASURING APPARATUS FOR CONTINUOUSLY AND WITHOUT CONTACT MEASURING THE THICKNESS OF A THIN CONDUCTING LAYER OF A RUNNING INSULATING SUPPORT SUCH AS A FIBER OR A TAPE

The present invention relates to apparatus for measuring continuously and without contact the thickness of a thin conducting layer on a running insulating support such as a fiber or a tape.

It relates particularly to measuring a deposit of carbon having a thickness of about 0.1 μm on a glass fiber having a diameter of 1.25 μm, which fiber is running along its own axis in a fiber-drawing machine at a speed lying in the range a few tens of meters per minute to a few hundreds of meters per minute.

BACKGROUND OF THE INVENTION

An optical method is known for measuring without contact the diameter of an optical fiber running through a laser beam. Measurement accuracy is about ±0.2 μm. Such a method could be considered for deposits having a thickness of more than 1 μm, but it is unsuitable for the thicknesses for which the present invention is intended.

U.S. Pat. No. 4,952,226 describes a method of that kind based on detecting laser light diffracted by a fiber, but the result of such measurement is greatly disturbed by lateral displacements of the fiber, which displacements are practically unavoidable in a fiber-drawing machine.

Commercially available measuring apparatuses are also known based on inducing eddy currents at very high frequency. Such apparatuses enable thicknesses greater than 5 μm to be measured on objects having a diameter of not less than 1 mm. Extrapolating the method implemented in such apparatuses to objects of smaller diameter provided with thinner deposits is not technically feasible.

An object of the present invention is to provide industrial apparatus enabling measurement to be performed without contact on a running fiber while preserving the mechanical strength of the fiber.

SUMMARY OF THE INVENTION

The present invention provides apparatus for measuring continuously and without contact the thickness of a thin conducting layer on a running insulating support of the fiber or tape kind, wherein the apparatus includes:

a microwave generator associated by coupling means with a resonant cavity comprising a metal wire in the form of a helix which is fixed at its ends to two metal plates, said insulating support being suitable for running substantially along the axis of said helix; and means for coupling said cavity to a detection device for detecting the transmission factor of said cavity, which factor is a direct function of said thickness, and said measurement being performed at constant frequency.

It is quite surprising to observe that when said support, and in particular an optical fiber, runs along the helix with its thin conducting layer, the resonance frequency of the cavity remains fixed. Only the amplitude of the signal varies as a function of the thickness of the layer. There is therefore no need to tune the frequency of the generator automatically while performing a measurement, which would require complex means to be implemented.

The said helix is preferably screened, i.e. enclosed in a metal container.

For an optical fiber having a diameter of 125 μm, and whose carbon layer is of the order of 0.1 μm to 0.05 μm thick, a helix can be used that is about 10 cm long, that is constituted by a metal wire, and that has an inside diameter of about 3 mm, with a pitch of about 2 mm to 3 mm.

In an advantageous embodiment, said microwave generator comprises a coaxial waveguide terminated by a dipole or a homopolar transmitting antenna suitable for transmitting in the direction of the electric field of said helix and compatible with resonance. The detection device comprises a receiving antenna that is analogous in structure to said transmitting antenna.

BRIEF DESCRIPTION OF THE DRAWINGS

An embodiment of the invention is described by way of example with reference to the accompanying drawings, in which.

DETAILED DESCRIPTION

Figure 1:
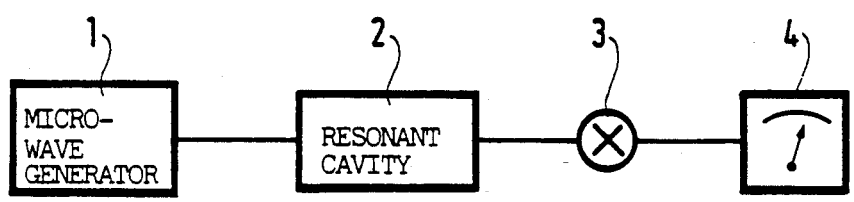
FIG. 1 is a highly simplified block diagram of apparatus of the invention.

FIG. 1 shows a microwave generator 1 coupled to a resonant cavity 2 whose transmission factor is measured by means of a detector 3 whose output is connected to a millivoltmeter 4.

Figure 2:
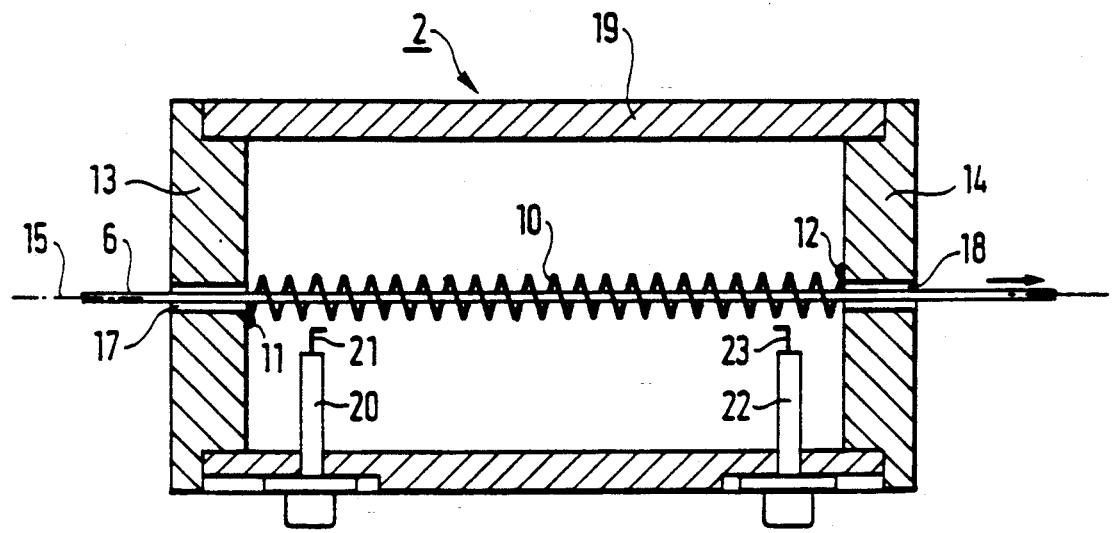
FIG. 2 is a diagrammatic view, partially in section, showing a resonant cavity used in the apparatus of FIG. 1.

The resonant cavity indicated generally at 2 (seen in greater detail in FIG. 2) comprises a helix 10 about an axis 15 constituted by a metal wire of silver or of silver-plated brass, and having a diameter of 0.3 mm. It has an inside diameter of 3 mm, a pitch of about 2 mm, and a length of 10 cm. Its ends 11 and 12 are fixed to two short circuit metal plates 13 and 14 in which openings 17 and 18 having a diameter of 2 mm to 3 mm are provided for passing an optical fiber 6 substantially on the axis 15. Ti is desirable for the helix 10 to be screened, i.e. for it to be enclosed in a metal-walled enclosure 19, e.g. a cylinder having a diameter of 30 mm coupled at opposite ends respectively to metal plates 13, 14, to which the opposite ends of metal helix 10 are fixed.

The microwave generator includes a coaxial waveguide 20 terminated by a monopole antenna 21 whose end extends parallel to the axis 15. The antenna 21 induces an electrical field in the direction corresponding to the desired resonance mode in the cavity 2. Because of this disposition, the field concentrates where the fiber 6 is going to run inside the helix. This parameter is extremely important for measurement accuracy.

The detector 3 includes a coaxial waveguide 22 with a receiving antenna 23 analogous to the waveguide 20 and the antenna 21. The antennas 21 and 23 should be microwave radiation coupled in the same way. The measurement result is read on a millivoltmeter 4.

Figure 3:
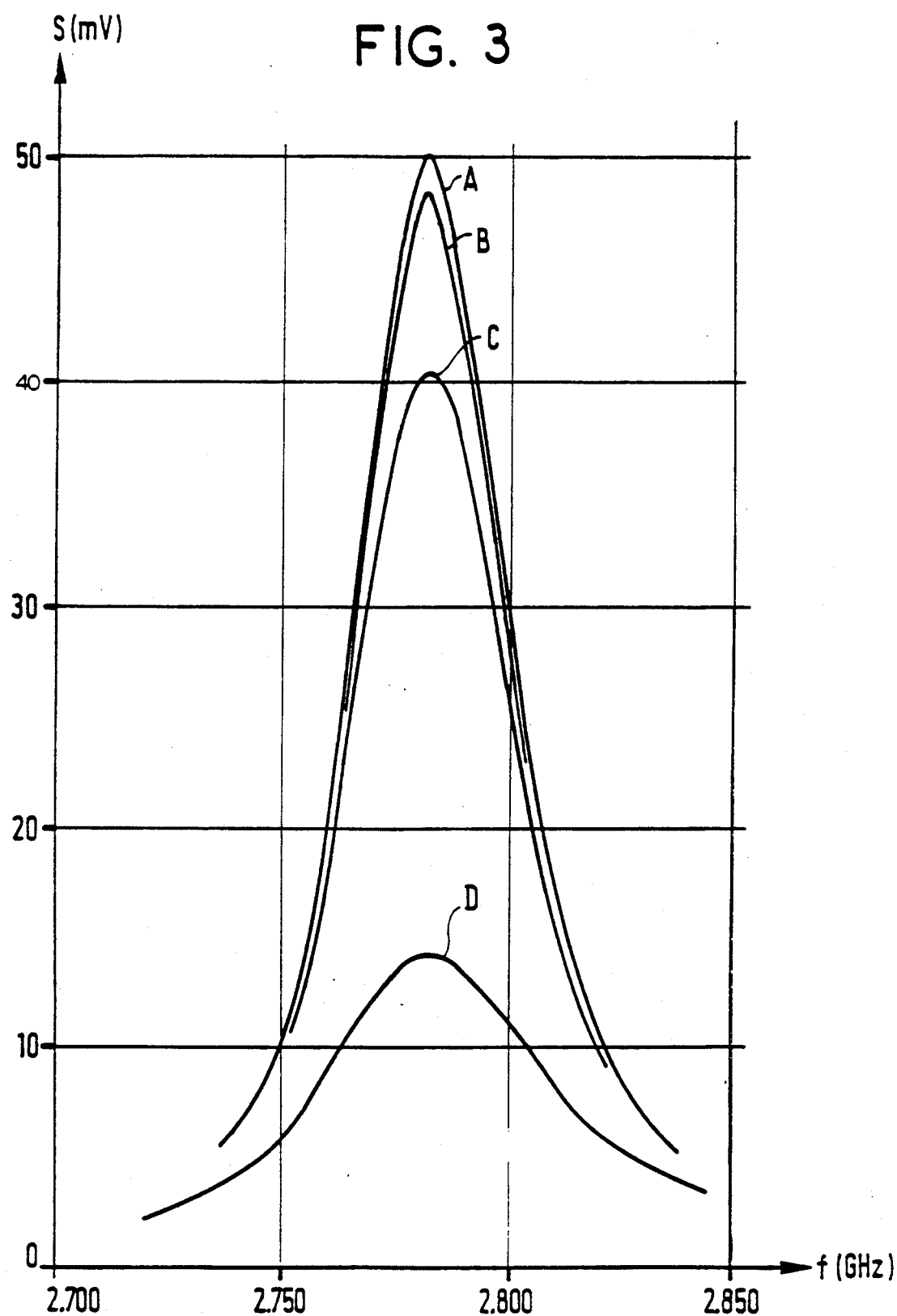
FIG. 3 is a graph showing the signal S (in mV) as measured at the output of the cavity of the invention as a function of the frequency f (in GHz) of the microwave generator, for fibers provided with various thicknesses of carbon layer.

If static fibers 6 provided with carbon layers of various thicknesses e are placed inside the helix 10, and if the frequency f of the generator is varied, a signal S is read (in mV) as plotted in FIG. 3.

Curve A corresponds to the cavity without a fiber. Curves B, C, and D correspond respectively to thicknesses e such that the corresponding resistances per unit length are 2500 kΩ/cm, 70 kΩ/cm, and 16 kΩ/cm.

Contrary to expectation, it can be seen that the resonant frequency remains the same regardless of whether or not there is a fiber inside the cavity. Nor does the frequency vary with the thickness of the layer of carbon on the fiber. In addition, it is observed that the amplitude of the signal does not depend on the lateral position of the fiber inside the helix 10 relative to the axis 15. The amplitude thus depends only on the thickness e of the layer. Measurement therefore requires no frequency resetting, thereby considerably simplifying the set up.

Figure 4:
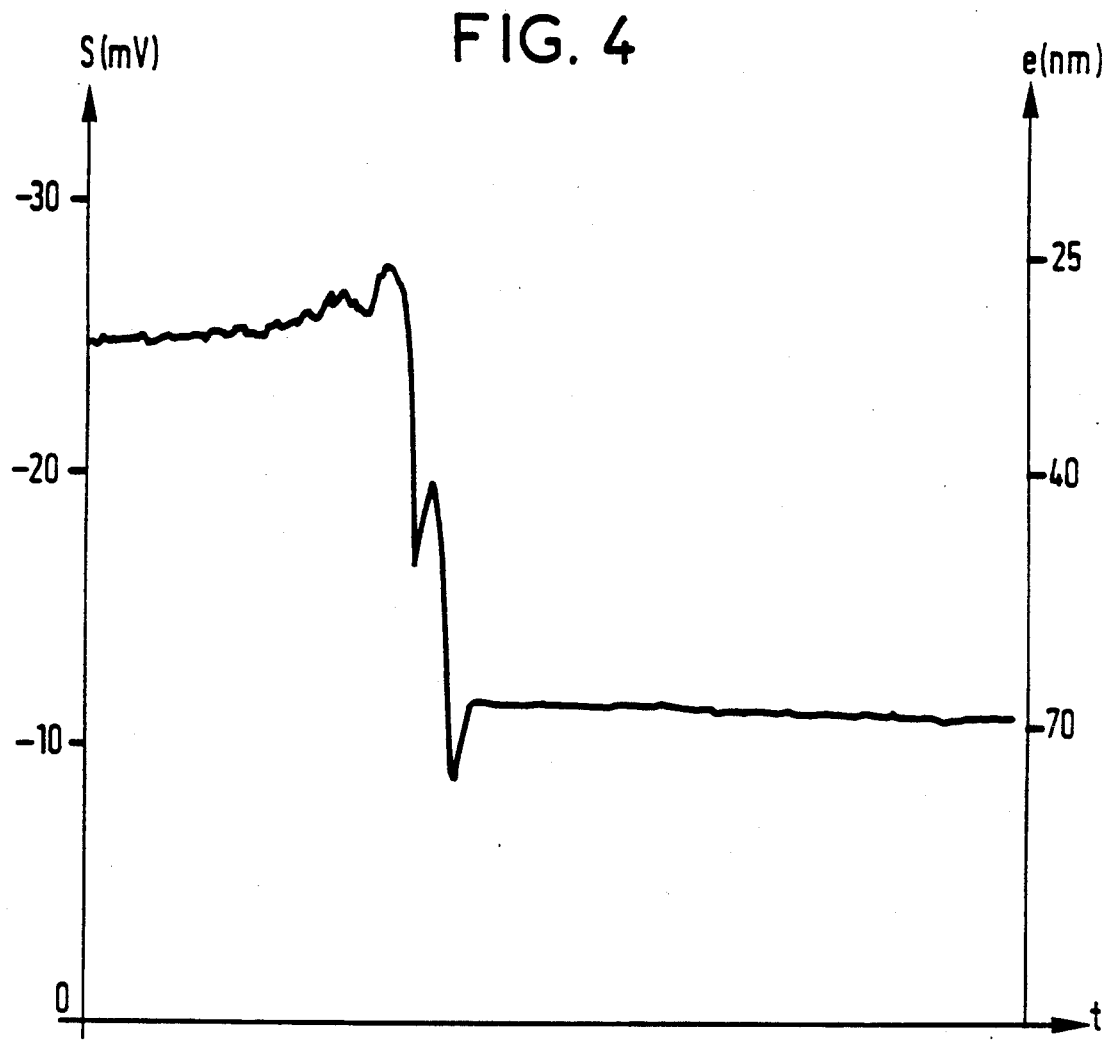
FIG. 4 is a graph showing how the measured signal S (in mV) varies as a fiber runs through a cavity of the invention.

FIG. 4 shows a recording of the signal S (in mV) as a function of fiber running time t. The second Y-axis converts the signal S into thickness e (in nanometers).

While the fiber is running, the measurement represents the mean value of the thickness along the fiber inside the helix 10. At a measurement speed of 5 meters per minute, the measurement is performed on about 20 cm of fiber. To maintain this definition at high speed, it is necessary to use a voltmeter having a higher passband, greater than 100 Hz for measurements at about 500 meters per minute.

In the example shown in FIG. 4, the mean thickness of the measured layer is about 30 nm, after which there occurs a sudden increase of thickness up to 70 nm, thereby giving rise to a significant drop in the signal S.

The measurement is very sensitive for thickness in the range of about 50 nm, corresponding to a resistance per unit length of 10 kΩ/cm to 30 kΩ/cm.

Figure 5:
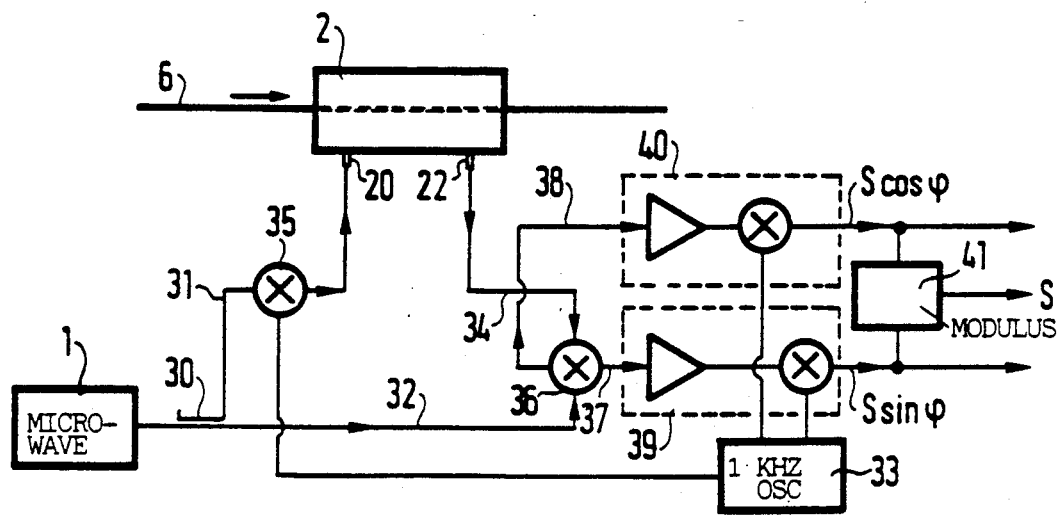
FIG. 5 is a block diagram of a variant apparatus of the invention.

Measurement sensitivity can be further increased by implementing the apparatus shown in FIG. 5.

This apparatus is recommended for measuring the complex transmission factor of the cavity 2 (i.e. both the amplitude and the phase of the signal S).

The signal from the generator 1 is split into two signals 31 and 32 by means of a directional coupler 30. The first signal 31 passes through an amplitude modulator 35 connected to an oscillator 33 (e.g. at 1 kHz) and penetrates into the cavity 2.

Both the second signal 32 used as a reference signal and the signal 34 detected at the output from the cavity 2 terminate in a balanced double mixer 36. The signals 37 and 38 therefrom are processed by two synchronous detectors 39 and 40 delivering two signals Ssinφ and Scosφ which determine the amplitude and the phase of the signal S. The amplitude S can be obtained directly by an analog circuit 41.

Naturally, the invention is not limited to the embodiments described above, whether they apply to signal processing or to the shape of the helix.

Thus, the helix could have turns that are rectangular in shape. It could be replaced by equivalent means adapted to the section of the insulating support passing through it.

We claim:

1. Microwave measuring apparatus for measuring continuously and without contact a thickness of a thin conducting layer on a running insulating support such as a fiber or tape, said apparatus comprising:
   a resonant cavity comprising a metal wire helix fixed at opposite ends respectively to two metal plates and being enclosed in a metal walled enclosure fixed to said two metal plates at opposite ends thereof, axial aligned openings provided in said two metal plates for passing said running insulating support substantially on the axis of said helix,
   a microwave generator operatively associated by first coupling means with said resonant cavity to induce an electrical field in a direction corresponding to a resonance mode in said resonant cavity, and
   a detection device operatively associated with second coupling means with said resonant cavity to detect a transmission factor of said cavity directly as a function of said thickness, whereby the resonant frequency remains the same regardless of whether or not there is a running insulating support inside the cavity, wherein the frequency is constant irrespective of the thickness of the conducting layer on the running support, wherein the amplitude of the measurement signal is unaffected by lateral position of the insulating support inside the helix relative to an axis thereof, with the amplitude of the signal depending only on the thickness of the layer and thereby eliminating the necessity for frequency resetting and considerably simplifying apparatus setup.

2. Microwave measuring apparatus according to claim 1, wherein said microwave generator comprises a coaxial waveguide terminated by a dipole or a homopolar transmitting antenna in juxtaposition to said helix for transmitting in the direction of the electric field of said helix and compatible with resonance.

3. Microwave measuring apparats according to claim 2, wherein said detection device comprises a receiving antenna structurally analogous to said transmitting antenna and in juxtaposition to said helix.

4. Microwave measuring apparatus according to claim 1, wherein, for an optical fiber constituting said running insulating support and having a diameter of 125 μm, and a carbon layer having a thickness on the order of 0.1 μm to 0.05 μm, said helix is constituted by a metal wire having an inside diameter of about 3 mm, a pitch of about 2 mm to 3 mm, and a length of about 10 mm.

5. Microwave measuring apparatus as claimed in claim 2, wherein said microwave generator coaxial waveguide is mounted to said metal walled enclosure.

6. Microwave measuring apparatus according to claim 3, wherein said detection device comprises a coaxial waveguide terminated by said receiving antenna and said coaxial waveguide is mounted to said metal walled enclosure.

* * * * *